US008197430B1

(12) United States Patent
Lentz

(10) Patent No.: US 8,197,430 B1
(45) Date of Patent: *Jun. 12, 2012

(54) METHOD AND SYSTEM TO REMOVE CYTOKINE INHIBITOR IN PATIENTS

(75) Inventor: M. Rigdon Lentz, Prien am Chiemsee (DE)

(73) Assignee: Biopheresis Technologies, Inc., Apex, NC (US)

( * ) Notice: Subject to any disclaimer, the term of this patent is extended or adjusted under 35 U.S.C. 154(b) by 2253 days.

This patent is subject to a terminal disclaimer.

(21) Appl. No.: 09/709,045

(22) Filed: Nov. 10, 2000

Related U.S. Application Data

(63) Continuation-in-part of application No. 09/699,003, filed on Oct. 26, 2000, now Pat. No. 7,854,717, which is a continuation of application No. 09/316,226, filed on May 21, 1999, now Pat. No. 6,231,536, which is a continuation-in-part of application No. 09/083,307, filed on May 22, 1998, now Pat. No. 6,620,382.

(60) Provisional application No. 60/164,695, filed on Nov. 10, 1999.

(51) Int. Cl.
*A61M 37/00* (2006.01)
*C02F 1/00* (2006.01)
*B01D 37/00* (2006.01)
*A61K 45/00* (2006.01)
*A61K 39/395* (2006.01)

(52) U.S. Cl. ............ 604/6.01; 604/5.01; 604/5.02; 604/5.03; 604/5.04; 604/6.04; 604/4.01; 604/8; 210/638; 210/645; 210/767; 424/85.1; 424/145.1; 128/898

(58) Field of Classification Search .............. 530/387.7, 530/388.2, 388.7, 389.6; 435/7.1, 7.2; 424/143.1
See application file for complete search history.

(56) References Cited

U.S. PATENT DOCUMENTS

| | | | |
|---|---|---|---|
| 4,116,589 A | 9/1978 | Rishton | |
| 4,189,470 A | 2/1980 | Rose | |
| 4,191,182 A | 3/1980 | Popovich et al. | |
| 4,350,156 A | 9/1982 | Malchesky et al. | |
| 4,362,155 A | 12/1982 | Skurkovich | |
| 4,375,414 A | 3/1983 | Strahilevitz | |
| 4,439,332 A | 3/1984 | Frank | |
| RE31,688 E | 9/1984 | Popovich et al. | |
| 4,486,282 A | 12/1984 | Bier | |
| 4,512,763 A * | 4/1985 | Schneider | 604/6.06 |
| 4,581,010 A | 4/1986 | Skurkovich et al. | |
| 4,605,394 A | 8/1986 | Skurkovich | |
| 4,614,513 A * | 9/1986 | Bensinger | 604/5.01 |
| 4,620,977 A | 11/1986 | Strahilevitz | |
| 4,633,417 A | 12/1986 | Wilburn et al. | |
| 4,634,417 A | 1/1987 | Korec | |
| 4,664,913 A | 5/1987 | Mielke et al. | |
| 4,708,713 A | 11/1987 | Lentz | |
| 4,787,974 A | 11/1988 | Ambrus et al. | |
| 4,801,449 A | 1/1989 | Balint, Jr. et al. | |
| 4,813,924 A | 3/1989 | Strahilevitz | |
| 4,824,432 A | 4/1989 | Skurkovich et al. | |
| 4,834,973 A | 5/1989 | Strahilevitz | |
| 4,863,611 A | 9/1989 | Bernstein | |
| 4,865,841 A | 9/1989 | Balint, Jr. et al. | |
| 4,963,265 A | 10/1990 | Okarma et al. | |
| 5,037,645 A | 8/1991 | Strahilevitz | |
| 5,037,649 A | 8/1991 | Balint, Jr. et al. | |
| 5,078,673 A | 1/1992 | Abrams | |
| 5,135,919 A | 8/1992 | Folkman et al. | |
| 5,147,638 A | 9/1992 | Esmon et al. | |
| 5,290,807 A | 3/1994 | Folkman et al. | |
| 5,340,736 A | 8/1994 | Goldberg et al. | |
| 5,356,374 A | 10/1994 | Hogan et al. | |
| 5,359,037 A | 10/1994 | Wallach | |
| 5,403,917 A | 4/1995 | Boos et al. | |

(Continued)

FOREIGN PATENT DOCUMENTS

CA 2107340 12/1992

(Continued)

OTHER PUBLICATIONS

Chen, at al., "Soluble TNF-a receptors are constitutively shed and downgregulate adhesion molecule expression in malignant gilomas," *J. Neuropathol. Exp. Neurol.* 56(5):541-550 (1997).

(Continued)

*Primary Examiner* — Cherie M Woodward
(74) *Attorney, Agent, or Firm* — Clark & Elbing LLP; Kristina Bieker-Brady

(57) ABSTRACT

A method to treat cancer uses ultrapheresis, refined to remove compounds of less than 120,000 daltons molecular weight, followed by administration of replacement fluid, to stimulate the patient's immune system to attack solid tumors. In the preferred embodiment, the patient is ultrapheresed using a capillary tube ultrafilter having a pore size of 0.02 to 0.05 microns, with a molecular weight cutoff of 120,000 daltons, sufficient to filter one blood volume. The preferred replacement fluid is ultrapheresed normal plasma. The patient is preferably treated daily for three weeks, diagnostic tests conducted to verify that there has been shrinkage of the tumors, then the treatment regime is repeated. The treatment is preferably combined with an alternative therapy, for example, treatment with an anti-angiogenic compound, one or more cytokines such as TNF, gamma interferon, or IL-2, or a procoagulant compound. The treatment increases endogenous, local levels of cytokines, such as TNF. This provides a basis for an improved effect when combined with any treatment that enhances cytokine activity against the tumors, for example, treatments using alkylating agents, doxyrubicin, carboplatinum, cisplatinum, and taxol. Alternatively, the ultrapheresis treatment can be combined with local chemotherapy, systemic chemotherapy, and/or radiation.

17 Claims, No Drawings

U.S. PATENT DOCUMENTS

| | | | |
|---|---|---|---|
| 5,523,096 A | 6/1996 | Okarma et al. | |
| 5,565,332 A * | 10/1996 | Hoogenboom et al. | 435/69.1 |
| 5,597,899 A | 1/1997 | Banner et al. | |
| 5,605,690 A | 2/1997 | Jacobs et al. | |
| 5,610,279 A | 3/1997 | Brockhaus | |
| 5,621,077 A | 4/1997 | Novick et al. | |
| 5,626,843 A | 5/1997 | Skurkovich et al. | |
| 5,629,327 A | 5/1997 | D'Amato | |
| 5,639,725 A | 6/1997 | O'Reilly et al. | |
| 5,643,732 A | 7/1997 | Strahilevitz | |
| 5,679,260 A | 10/1997 | Boos et al. | |
| 5,698,586 A | 12/1997 | Kishimoto et al. | |
| 5,705,615 A | 1/1998 | Lim et al. | |
| 5,712,291 A | 1/1998 | D'Amato | |
| 5,713,491 A | 2/1998 | Hughes et al. | |
| 5,716,981 A | 2/1998 | Hunter et al. | |
| 5,730,713 A | 3/1998 | Okarma et al. | |
| 5,733,876 A | 3/1998 | O'Reilly et al. | |
| 5,736,138 A | 4/1998 | Pfizenmaier et al. | |
| 5,753,227 A | 5/1998 | Strahilevitz | |
| 5,792,845 A | 8/1998 | O'Reilly et al. | |
| 5,808,029 A | 9/1998 | Brockhaus | |
| 5,817,522 A | 10/1998 | Goodman et al. | |
| 5,817,528 A * | 10/1998 | Bohm et al. | 436/529 |
| 5,840,588 A | 11/1998 | Strahilevitz | |
| 5,861,483 A | 1/1999 | Wolpe | |
| 5,869,047 A | 2/1999 | Blake | |
| 5,888,511 A | 3/1999 | Skurkovich et al. | |
| 5,910,252 A | 6/1999 | Truitt et al. | |
| 5,919,898 A | 7/1999 | Nakatani et al. | |
| 5,925,633 A | 7/1999 | Singh et al. | |
| 5,932,704 A | 8/1999 | Jubinsky | |
| 5,965,394 A | 10/1999 | Bandman et al. | |
| 5,980,887 A | 11/1999 | Isner et al. | |
| 6,017,527 A | 1/2000 | Maraskovsky et al. | |
| 6,039,946 A | 3/2000 | Strahilevitz | |
| RE36,755 E | 6/2000 | Smith et al. | |
| 6,133,431 A | 10/2000 | Yasuda | |
| 6,197,289 B1 | 3/2001 | Wirt et al. | |
| 6,221,614 B1 | 4/2001 | Prusiner et al. | |
| 6,231,536 B1 | 5/2001 | Lentz | |
| 6,232,446 B1 | 5/2001 | Wallach | |
| 6,245,038 B1 | 6/2001 | Borberg et al. | |
| 6,262,127 B1 | 7/2001 | Acemoglu et al. | |
| 6,264,623 B1 | 7/2001 | Strahilevitz | |
| 6,287,516 B1 | 9/2001 | Matson et al. | |
| 6,379,708 B1 | 4/2002 | Howell et al. | |
| 6,428,790 B1 | 8/2002 | Boyd | |
| 6,432,405 B1 | 8/2002 | Weinberg et al. | |
| 6,528,057 B1 | 3/2003 | Ambrus et al. | |
| 6,561,997 B1 | 5/2003 | Weitzel et al. | |
| 6,569,112 B2 | 5/2003 | Strahilevitz | |
| 6,602,502 B1 | 8/2003 | Strahilevitz | |
| 6,602,993 B2 | 8/2003 | Wallach et al. | |
| 6,607,501 B2 | 8/2003 | Gorsuch | |
| 6,607,723 B1 | 8/2003 | Good et al. | |
| 6,620,382 B1 * | 9/2003 | Lentz | 422/44 |
| 6,627,151 B1 | 9/2003 | Borberg et al. | |
| 6,630,315 B1 | 10/2003 | Miwa et al. | |
| 6,676,622 B2 | 1/2004 | Strahilevitz | |
| 6,685,664 B2 | 2/2004 | Levin et al. | |
| 6,720,155 B1 | 4/2004 | Lopez et al. | |
| 6,774,102 B1 | 8/2004 | Bell et al. | |
| 6,824,986 B1 | 11/2004 | Finkelman et al. | |
| 6,866,846 B1 | 3/2005 | Heinrich et al. | |
| 6,878,127 B2 | 4/2005 | Brady et al. | |
| 6,982,089 B2 | 1/2006 | Tobinick | |
| 7,105,484 B2 | 9/2006 | Klein et al. | |
| 7,196,070 B2 | 3/2007 | Sukumar | |
| 7,238,776 B2 | 7/2007 | Hauptmann | |
| 7,368,295 B2 | 5/2008 | Tovar et al. | |
| 2001/0010818 A1 | 8/2001 | Engle et al. | |
| 2001/0039392 A1 | 11/2001 | Strahilevitz | |
| 2002/0019603 A1 | 2/2002 | Strahilevitz | |
| 2002/0058031 A1 | 5/2002 | Tung et al. | |
| 2002/0086276 A1 | 7/2002 | Srivastava | |
| 2002/0107469 A1 | 8/2002 | Bolan et al. | |
| 2002/0111577 A1 | 8/2002 | Sirimanne et al. | |
| 2002/0114728 A1 | 8/2002 | Kulish et al. | |
| 2002/0119147 A1 | 8/2002 | Howell et al. | |
| 2002/0159995 A1 | 10/2002 | Brady et al. | |
| 2002/0183677 A1 | 12/2002 | Chang et al. | |
| 2002/0187069 A1 | 12/2002 | Levin et al. | |
| 2002/0197249 A1 | 12/2002 | Brady et al. | |
| 2002/0197250 A1 | 12/2002 | Brady et al. | |
| 2002/0197251 A1 | 12/2002 | Brady et al. | |
| 2003/0073822 A1 | 4/2003 | Lofling et al. | |
| 2003/0118584 A1 | 6/2003 | Glenn et al. | |
| 2003/0125657 A1 | 7/2003 | Koll et al. | |
| 2003/0127390 A1 | 7/2003 | Davis, Jr. | |
| 2003/0129130 A1 | 7/2003 | Guire et al. | |
| 2003/0133929 A1 | 7/2003 | Cham | |
| 2003/0138349 A1 | 7/2003 | Robinson et al. | |
| 2003/0148404 A1 | 8/2003 | Michaelson | |
| 2003/0163077 A1 | 8/2003 | Kim et al. | |
| 2003/0195452 A1 | 10/2003 | Hunley et al. | |
| 2003/0215443 A1 | 11/2003 | Coffey et al. | |
| 2004/0044301 A1 | 3/2004 | Levin et al. | |
| 2004/0054315 A1 | 3/2004 | Levin et al. | |
| 2005/0244371 A1 | 11/2005 | Lentz | |
| 2005/0265996 A1 | 12/2005 | Lentz | |
| 2007/0065514 A1 | 3/2007 | Howell et al. | |
| 2008/0057060 A1 | 3/2008 | Lentz | |
| 2008/0075690 A1 | 3/2008 | Howell et al. | |
| 2008/0145333 A1 | 6/2008 | Lentz | |
| 2008/0275376 A1 | 11/2008 | Howell et al. | |

FOREIGN PATENT DOCUMENTS

| | | |
|---|---|---|
| DE | 3302384 | 1/1983 |
| DE | 43 45 200 | 12/1994 |
| DE | 196 24 250 | 1/1998 |
| EP | 0 184 040 | 6/1986 |
| EP | 0076665 | 1/1987 |
| EP | 289896 | 7/1992 |
| EP | 334165 | 12/1995 |
| EP | 787500 | 12/1999 |
| EP | 589982 | 1/2001 |
| GB | 2136314 | 9/1984 |
| JP | 56092824 | 7/1981 |
| JP | 02045064 | 2/1990 |
| JP | 6 296860 | 10/1994 |
| RU | 2 130 069 | 5/1999 |
| WO | WO 79/01121 | 12/1979 |
| WO | WO 90/09798 | 9/1990 |
| WO | WO 9100742 | 1/1991 |
| WO | WO 91/09967 | 7/1991 |
| WO | WO 93/12142 | 6/1993 |
| WO | WO 94/09137 | 4/1994 |
| WO | WO 94/26924 | 11/1994 |
| WO | WO 96/16666 | 6/1996 |
| WO | WO 97/14964 | 4/1997 |
| WO | WO 98/17799 | 4/1998 |
| WO | WO 98/28001 | 7/1998 |
| WO | WO 99/61085 A | 12/1999 |
| WO | WO 01/37873 | 5/2001 |
| WO | WO 03/056896 | 7/2003 |
| WO | WO 2005/037865 | 4/2005 |
| WO | WO 2006/002151 | 1/2006 |
| WO | WO 2008/115597 | 9/2008 |

OTHER PUBLICATIONS

Clackson, et al., "Making antibody fragments using phage display libraries," *Nature* 352:624-688 (1991).

Daugherty, et al., "Polymerase chain reaction facilitates the cloning, CDR-grafting, and rapid expression of a , murine monoclonal antibody directed against the CD18 component of leukocyte integrins," *Nucl. Acids Res.* 19:2471-2476 (1991).

Ey, et al., "Isolation of pure $IgG_1$, $IgG_{2a}$, and $IgG_{2b}$, immunoglobulins from mouse serum using protein A-Sepharose," *Immunochemistry* 15:429-436 (1978).

Feinman, et al., "Tumor necrosis factor is a important mediator of tumor cell killing by human monocytes," *J Immunol* 138:635 (1987).

*Hemostasis and Thrombosis: Basic Principles and Clinical Practice* 2nd Ed., Colman, R.W., et al.,p. 263 (J.B.Lippincott, Philadelphia, PA 1987).

Howard, et al., "Vaccinia virus homologues of the *Shope fibroma* virus inverted terminal repeat proteins and a discontinuous ORF related to the tumor necrosis factor receptor family," *Virology* 180:633-664 (1991).

Gatanaga, et al., "Purification and characterization of an inhibitor (soluble tumor necrosis factor receptor) for tumor necrosis factor and lymphotoxin obtained from the serum ultrafiltrates of human cancer patients," *Proceedings of the National Academy of the USA* 87(22):8781-87814 (1990).

Lentz, "Continuous whole blood Ultra Pheresis procedure in patients with metastatic cancer," *Journal of Biological Response Modifiers* 8(5):511-527 (1989).

Aderka, et al., "Increased serum levels of soluble receptors for tumor necrosis factor in cancer patients," *Cancer Res.* 51: 5602-5607 (1991).

Amit, et al., "Three-dimensional structure of an antigen-antibody complex at 2.8 resolution," *Science* 233: 747-751 (1986).

Digel, et al., "High levels of circulating soluble receptors for tumor necrosis factor in hairy cell leukemia and type B chronic lymphocytic leukemia," *J. Clin. Invest* 89: 1690-1693 (1992).

Elsässer-Beile, et al., "Increased plasma concentrations for type I and II tumor necrosis factor receptors and IL-2 receptors in cancer patients," *Tumor Biol.* 15: 17-24 (1993).

Kessler, "Adsorptive plasma treatment: optimization of extracorporeal devices and systems," *Blood Purif.* 11: 150-157 (1993).

Lentz, et al., "Low molecular weight protein apheresis and regression of breast cancer," *Jpn. J. Apheresis* 16(1): 107-114 (1997).

Panka, et al., "Variable region framework differences result in decreased or increased affinity of variant anti-digoxin antibodies," Proc. Natl. Acad. Sci. USA 85: 3080-3084 (1988).

Rudikoff, et al., "Single amino acid substitution altering antigen-binding specificity," *Immunology* 79: 1979-1983 (1982).

Selinsky & Howell, "Soluble tumor necrosis factor receptor type I enhances tumor development and persistence in vivo," *Cell. Immunol.* 200: 81-87 (2000).

Selinsky, "Dissertation: The role of soluble tumor necrosis factor type I in tumor survival," Colorado State University, Fort Collins, Colorado (1999).

Gerain, et al., "Systemic release of soluble TNF receptors after high-dose TNF in isolated limb perfusion" *Cytokine* 9(12):1034-1042 (1997).

Abbruzzese, et al., "A phase II trial of recombinant human interferon-gamma and recombinant tumor necrosis factor in patients with advanced gastrointestinal malignancies: Results of a trial terminated by excessive toxicity" *Journal of Biological Response Modifiers* 9:522-527 (1990).

Adolf and Apfler, "A monoclonal antibody-based enzyme immunoassay for quantitation of human tumor necrosis factor binding protein I, a soluble fragment of the 60kDa TNF receptor, in biological fluids" *J. Immunol. Meth.* 143:127-136 (1991).

Ajani, et al., "Phase I and II studies of the combination of recombinant human interferon-γ and 5-fluorouracil in patients with advanced colorectal carcinoma" *Journal of Biological Response Modifiers* 8:140-146 (1989).

Albertini, et al., "Limiting dilution analysis of lymphokine-activated killer cell precursor frequencies in peripheral blood lymphocytes of cancer patients receiving interleukin-2 therapy" *Journal of Biological Response Modifiers* 9:456-462 (1990).

Arend, "Inhibiting the effects of cytokines in human diseases" *Adv. Int. Med.* 40:365-394 (1995).

Avner, et al., "Therapeutic murine monoclonal antibodies developed for individual cancer patients" *Journal of Biological Response Modifiers* 8:25-36 (1989).

Balcewicz-Sablinska, et al., "Pathogenic *Mycobacterium tuberculosis* evades apoptosis of host macrophages by release of TNF-R2, resulting in inactivation of TNF-α" *J. Immunol.* 161:2636-2641 (1998).

Baliko, et al., "Th2 biased immune response in cases with active *Mycobacterium tuberculosis* infection and tuberculin anergy" *FEMS Immunol. Med. Micro.* 22:188-204 (1998).

Bermudez and Champsi, "Infection with *Mycobacterium avium* induces production of interleukin-10 (IL-10), and administration of anti-IL-10 antibody is associated with enhanced resistance to infection in mice" *Infect. Immun.* 61:3093-3097 (1993).

Beutler and Cerami, "The biology of cachectin/TNF-A primary mediator of the host response". *Ann. Rev. Immunol.* 7:625-655 (1989).

Blauer, et al., "Modulation of the antilisterial activity of human blood-derived macrophages by activating and deactivating cytokines" *J. Interferon Cytokine Res.* 15:105-114 (1995).

Boman, et al., "Phase I study of recombinant gamma-interferon (rIFN-γ)" *Journal of Biological Response Modifiers* 7:438-446 (1988).

Bruntsch, et al., "phase II study of recombinant human interferon-γ in metastatic renal cell carcinoma" *Journal of Biological Response Modifiers* 9:335-338 (1990).

Bukowski, et al., "Phase I trail of continuous infusion of recombinant interleukin-2 and intermittent recombinant interferon-$\alpha_{2a}$. Clinical effects" *Journal of Biological Response Modifiers* 9:538-545 (1990).

Caulfield, et al., "Phase I1-Ib trial of an anti-$G_{D3}$ monoclonal antibody in combination with interferon-α in patients with malignant melanoma" *Journal of Biological Response Modifiers* 9:319-328 (1990).

Chambrier, et al., "Hormonal and metabolic effects of chronic interleukin-2 infusion in cancer patients" *Journal of Biological Response Modifiers* 9:251-255 (1990).

Chouaib, et al., "More insights into the complex physiology of TNF" *Immunol. Today* 12(5):141-145 (1991).

Coclet-Ninin, et al., "Interferon-beta not only inhibits interleukin-1β and tumor necrosis factor-α but stimulates interleukin-1 receptor antagonist production in human peripheral blood mononuclear cells" *Eur. Cytokine Network* 8(4):345-349 (1997).

Colman, et al., *Hemostatsis and Thrombosis: Basic Principles and Clinical Practice 2nd. Edition* (Colman, et al., eds.) pp. 63-67 J.B. Lippincott: Philadelphia, PA, 1987.

Cox, et al., "Phase II study of human lymphoblastoid interferon in patients with multiple myeloma" *Journal of Biological Response Modifiers* 7:318-325 (1988).

Creaven, et al., "Initial clinical trial of the macrophage activator muramyl tripeptide-phosphatidylethanolamine encapsulated in liposomes in patients with advanced cancer" *Journal of Biological Response Modifiers* 9:492-498 (1990).

Croghan, et al., "A phase I trial of recombinant interferon-α and α-difluoromethylornithine in metastatic melanoma" *Journal of Biological Response Modifiers* 7:409-415 (1988).

D'Andrea, et al., "Interleukin 10 (IL-10) inhibits human lymphocyte interferon γ production by suppressing natural killer cell stimulatory factor/IL-12 synthesis in accessory cells" *J. Exp. Med.* 178:1041-1048 (1993).

Dimery, et al., "Recombinant interferon-γ in the treatment of recurrent nasopharyngeal carcinoma" *Journal of Biological Response Modifiers* 8:221-226 (1989).

Dinarello, "Induction of interleukin-I and interleukin-I receptor antagonist" *Sem. In Oncol.* 24(No. 3, Suppl. 9):81-93 (1997).

Dupere, et al., "Patterns of cytokines released by peripheral blood leukocytes of normal donors and cancer patients during interleukin-2 activation in vitro" *Journal of Biological Response Modifiers* 9:140-148 (1990).

Engelhardt, et al, "Biological response to intravenously administered endotoxin in patients with advanced cancer" *Journal of Biological Response Modifiers* 9:480-491 (1990).

Engelmann, et al., "Two tumor necrosis factor-binding proteins purified from human urine" *J. Biol. Chem.* 265(3):1531-1536 (1990).

Eriks and Emerson, "Temporal effect of tumor necrosis factor alpha on murine macrophages infected with *Mycobacterium avium*" *Infect. Immun.* 65(6):2100-2106 (1997).

Etges and Muller, "Progressive disease or protective immunity to *Leishmania* major infection: the result of a network of stimulatory and inhibitory interactions" *J. Mol. Med.* 76:372-390 (1998).

Fareed, et al., "Novel antigenic markers of human tumor regression" *Journal of Biological Response Modifiers* 7:11-23 (1988).

Favrot, et al., "Functional and immunophenotypic modifications induced by interleukin-2 did not predict response to therapy in patients with renal cell carcinoma" *Journal of Biological Response Modifiers* 9:167-177 (1990).

Fernandes and Baldwin, "Interleukin-10 downregulates protective immunity to *Brucella abortus*" *Infect. Immun.* 63:1130-1133 (1995).

Foon, et al., "A prospective randomized trial of $\alpha_{2B}$-interferon/$\gamma$-interferon or the combination in advanced metastatic renal cell carcinoma" *Journal of Biological Response Modifiers* 7:540-545 (1988).

Frost, et al., "Interleukin-6 induction by a muramyltripeptide derivative in cancer patients" *Journal of Biological Response Modifiers* 9:160-166 (1990).

Gadducci, et al., "Serum levels of soluble receptors for tumor necrosis factor (p55 and p75 sTNFr) in endometrial cancer" *Anticancer Res.* 16:3125-3128 (1996).

Gill, et al., "Interferon-alpha maintenance therapy after cytotoxic chemotherapy for treatment of acquired immunodeficiency syndrome-related kaposi's sarcoma" *Journal of Biological Response Modifiers* 9:512-516 (1990).

Greenblatt, et al., "The type B receptor for tumor necrosis factor-alpha" *Blood* 80:1339-1346 (1992).

Gustavson, et al., "Pharmacokinetics of teceleukin (Recombinant human inteleukin-2) after intravenous or subcutaneous administration to patients with cancer" *Journal of Biological Response Modifiers* 8:440-449 (1989).

Handzel, et al., "Immunomodulation of T cell deficiency in humans by thymic humoral factor: from crude extract to synthetic thymic humoral factor-$\gamma$2" *Journal of Biological Response Modifiers* 9:269-278 (1990).

Hank, et al., "Depressed in vitro T cell responses concomitant with augmented interleukin-2 responses by lymphocytes from cancer patients following in vivo treatment with interleukin-2" *Journal of Biological Response Modifiers* 9:5-14 (1990).

Hercend, et al., "Immunotherapy with lymphokine-activated natural killer cells and recombinant interleukin-2: A feasibility trial in metastatic renal cell carcinoma" *Journal of Biological Response Modifiers* 9:546-555 (1990).

Herrmann, et al., "Stimulation of granulopoiesis in patients with malignancy by recombinant human granulocyte-macrophage colony-stimulating factor: Assessment of two routes of administration" *Journal of Biological Response Modifiers* 9:475-479 (1990).

Hertler, et al., "A phase I study of T101-ricin A chain immunotoxin in refractory chronic lymphocytic leukemia" *Journal of Biological Response Modifiers* 7:97-113 (1988).

Himmler, et al., "Molecular cloning and expression of human and rat tumor necrosis factor receptor chain (p60) and its soluble derivative, tumor necrosis factor-binding protein" *DNA and Cell Biol.* 9(10):705-715 (1990).

Jacobs, et al., "minimal antigenicity of intron A in human recipients demonstrated by three analytical methods" *Journal of Biological Response Modifiers* 7:447-456 (1988).

Jakobsen, et al., "Decreased antitoxic activities among children with clinical episodes of malaria" *Infect. Immun.* 66(4):1654-1659 (1998).

Jakschies, et al., "Emergence and decay of the human Ms homolog in cancer patients during and after interferon-$\alpha$ therapy" *Journal of Biological Response Modifiers* 9:305-312 (1990).

Kalmanti, et al., "Serum levels of tumor necrosis factor soluble interleukin 2 receptor as markers of disease activity and prognosis in childhood leukemia and lymphoma" *Int. J. Hematol.* 57:147-152 (1993).

Kaufmann, et al., "T cells and cytokines in intracellular bacterial infections: experiences with *Mycobacterium bovis* BCG" *Ciba Fdn. Symp.* 195:123-132 (1995).

Kellokumpu-Lehtinen, et al., "Recombinant interferon-$\alpha$2a and vinblastine in advanced renal cell cancer: A clinical phase I-II study" *Journal of Biological Response Modifiers* 9:439-444 (1990).

Kessler, "Adsorptive plasma treatment: Optimization of extracorporeal devices and systems" *Blood Purification* 11:150-157 (1993).

Khazaeli, et al., "Initial evaluation of a human immunoglobulin M monoclonal antibody (HA-1A) in humans" *Journal of Biological Response Modifiers* 9:178-184 (1990).

Kolitz, et al., "Phase I trial of recombinant interleukin-2 and cyclophosphamide: Augmentation of cellular immunity and T-cell mitogenic response with long term administration of rIL-2" *Journal of Biological Response Modifiers* 7:457-472 (1988).

Krigel, et al., "Treatment of epidemic kaposi's sarcoma with a combination of interferon-alpha 2b and etoposide" *Journal of Biological Response Modifiers* 7:359-364 (1988).

Lantz, et al., "Infusion of tumor necrosis factor (TNF) causes an increase in circulating TNF-binding protein in humans" *Cytokine* 2(6):402-406 (1990).

Laszlo, et al., "Phase I studies of recombinant interferon-$\gamma$" *Journal of Biological Response Modifiers* 9:185-193 (1990).

Laucella, et al., "Papel de las citoquinas en la resistencia y patologia durante la infeccion con *Trypanosome cruzi*" *Revista Argentina de Microbiologia*, 28:99-109 (1996).

Lentz, et al., "Apheresis of low molecular weight protein fraction and the onset of labor" *Journal of Clinical Apheresis* 5:62-67 (1990).

Lentz, "The phylogeny of oncology" *Mol. Biother.* 2:137-144 (1990).

Letterio and Roberts, "Regulation of immune responses by TGF-$\beta$" *Ann. Rev. Immuno.* 16:137-161 (1998).

Litton, et al., "Biological and clinical effects of the oral immunomodulator 3,6'Bis(2-piperidinoethoxy)acridine trihydrochloride in patients with malignancy" *Journal of Biological Response Modifiers* 9:61-70 (1990).

Lucey, et al., "Type 1 and type 2 cytokine dysregulation in human infectious, neoplastic, and inflammatory diseases" *Clin. Micro. Rev*, 9(4):532-562 (1996).

Maas, et al., "Interleukin-2 in cancer treatment: disappointing or (still) promising? A review" *Cancer Immunol. Immunother.* 36:141-148 (1993).

Maca, "Inhibition of the growth of lewis lung carcinoma by indomethacin in conventional, nude, and beige mice" *Journal of Biological Response Modifiers* 9:568-580 (1990).

Marshall, et al., "Effects of coumarin (12-benzopyrone) and cimetidine on peripheral blood lymphocytes, natural killer cells, and monocytes in patients with advanced malignancies" *Journal of Biological Response Modifiers* 8:62-69 (1989).

Marshall, et al., "Treatment of renal cell carcinoma with daily low-dose alpha-interferon" *Journal of Biological Response Modifiers* 8:453-461 (1989).

Miles, et al., "induction of soluble tumour necrosis factor receptors during treatment with interleukn-2" *Brit. J. Cancer* 66:1195-1199 (1992).

Mittelman, et al., "Treatment of patients with advanced cancer using multiple long-term cultured lymphokine-activatied killer (LAK) cell infusions and recombinant human interleukin-2" *Journal of Biological Response Modifiers* 8:468-478 (1989).

Musiani, et al., "Effect of low doses of interleukin-2 injected perilymphatically and peritumorally in patients with advanced primary head and neck squamous cell carcinoma" *Journal of Biological Response Modifiers* 8:571-578 (1989).

Neidhart, "Phase I study of recombinant methionyl human consensus interferon (r-metHulFN-Con)" *Journal of Biological Response Modifiers* 7:240-248 (1988).

Oratz, et al. "Induction of tumor-infiltrating lymphocytes in human malignant melanoma metastases by immunization to melanoma antigen vaccine" *Journal of Biological Response Modifiers* 8:355-358 (1989).

Oratz, et al., "Antimelanoma monoclonal antibody-ricin a chain immunoconjugate (XMMME-001-RTA) plus cyclophosphamide in the treatment of metastatic malignant melanoma: Results of a phase II trial" *Journal of Biological Response Modifiers* 9:345-354 (1990).

Pais, et al., "Pharmacokinetics of recombinant interleukin-2 in children with malignancies: A pediatric oncology group study" *Journal of Biological Response Modifiers* 9:517-521 (1990).

Paolozzi, et al., "Phase I trial of recombinant interleukin-2 and recombinant $\beta$-interferon in refractory neoplastic diseases" *Journal of Biological Response Modifiers* 8:122-139 (1989).

Perez, et al., "A phase I trial of recombinant human gamma interferon (IFN-$\gamma_{4A}$) in patients with advanced malignancy" *Journal of Biological Response Modifiers* 7:309-317 (1988).

Quesada, et al., "Recombinant interferon alpha and gamma in combination as treatment for tetastatic renal cell carcinoma" *Journal of Biological Response Modifiers* 7:234-239 (1988).

Rabinowitz, et al., "Hemolytic anemia in a cancer patient treated with recombinant interferon-γ" *Journal of Biological Response Modifiers* 9:256-259 (1990).

Reimann, et al., "Suppression of the immune response by microorganisms" *Scand. J. Immunol.* 31:543-546 (1990).

Riffkin, et al., "Defense against the immune barrage: helminth survival strategies" *Immunol. Cell Bio* 74:564-574 (1996).

Romani, et al., "T helper cell dichotomy to *Candida albicans*: implications for pathology" *Immunol. Res.* 14:148-162 (1995).

Rosenthal, et al., "The in vitro function of lymphocytes from 25 cancer patients receiving four to seven consecutive days of recombinant IL-2" *Journal of Biological Response Modifiers* 7:123-139 (1988).

Rybak, et al., "Interferon therapy of relapsed and refractory hodgkin's disease: Cancer and leukemia group B study 8652" *Journal of Biological Response Modifiers* 9:1-4 (1990).

Sarna, et al., "Systemic administration of recombinant methionyl human interleukin-2 (Ala 125) to cancer patients: Clinical results" *Journal of Biological Response Modifiers* 8:16-24 (1989).

Sarna, et al., "A pilot study of intralymphatic interleukin-2. II. Clinical and biological effects" *Journal of Biological Response Modifiers* 9:81-86 (1990).

Sarthou, et al., "Prognostic value of anti-*Plasmodium falciparum*-specific immunoglobulin G3, cytokines, and their soluble receptors in west African patients with severe malaria" *Infect. Immun.* 65(8):3271-3276 (1997).

Sato, et al., "induction of bone formation in an adenoid cystic carcinoma of the maxillary sinus by adoptive immunotherapy involving intra-arterial injection of lympholine-activated killer cells and recombinant interleukin-2 in combination with radiotherapy" *Journal of Biological Response Modifiers* 9:329-334 (1990).

Schaadt, et al., "Phase II study of recombinant human tumor necrosis factor in colorectal carcinoma" *Journal of Biological Response Modifiers* 9:247-250 (1990).

Schall, et al., "molecular cloning and expression of a receptor for human tumor necrosis factor" *Cell* 61:361-370 (1990).

Scheithauer, et al., "Combined α-2C-interferon/VMCP polychemotherapy versus VMCP polychemotherapy a induction therapy in multiple myeloma: A prospective randomized trial" *Journal of Biological Response Modifiers* 8:109-115 (1989).

Schiller, et al., "A phase I trial of interferon-α-2a plus cyclophosphamide, vincristine, prednisone, and doxorubicin" *Journal of Biological Response Modifiers* 8:252-261 (1989).

Seckinger, et al., "Purification and biologic characterization of a specific tumor necrosis factor α inhibitor" *J. Biol. Chem.* 264(20):11966-11973 (1989).

Seigler, et al, "Melanoma patient antibody responses to melanoma tumor-associated antigens defined by murine monoclonal antibodies" *Journal of Biological Response Modifiers* 8:37-52 (1989).

Shau, et al., "A pilot study of intralymphatic interleukin-2. I. Cytotoxic and surface marker changes of peripheral blood lymphocytes" *Journal of Biological Response Modifiers* 9:71-80 (1990).

Sidhu and Bollon, "Tumor necrosis factor activities and cancer therapy—A perspective" *Pharmacol. Ther.* 57:79-128 (1993).

Sieling, et al., "Immunosuppressive roles for IL-10 and IL-4 in human infection" *J. Immunol.* 150(12):5501-5510 (1993).

Spriggs, "One step ahead of the game: Viral immunomodulatory molecules" *Ann. Rev. Immunol.* 14:101-130 (1996).

Steger, et al., "Long-term remission in a patient with erythroleukemia following interferon-α treatment" *Journal of Biological Response Modifiers* 8:351-354 (1989).

Steinmetz, et al., "Phase I study of 24-hour continuous intravenous infusion of recombinant human tumor necrosis factor" *Journal of Biological Response Modifiers* 7:417-423 (1988).

Sznol, et al., "A phase I study of high-dose interleukin-2 in combination with interferon $\alpha_{2b}$," *Journal of Biological Response Modifiers* 9:529-537 (1990).

Trigg, et al., "α-interferon therapy for lymphoproliferative disorders developing in two children following bone marrow transplants" *Journal of Biological Response Modifiers* 8:603-613 (1989).

Trinchieri, et al., "Cytokine cross-talk between phagocytic cells and lymphocytes: Relevance for differentiation/Activation of phagocytic cells and regulation of adaptive immunity" *J. Cell. Biochem.* 53:301-308 (1993).

Trump et al., "Interferon-α-n1 and continuous infusion vinblastine for treatment of advanced renal cell carcinoma" *Journal of Biological Response Modifiers* 9:108-111 (1990).

Umiel, et al., "Recombinant interleukin-2-activated intracavitary lymphocytes: Phenotypic characteristics and effector function" *Journal of Biological Response Modifiers* 8:409-421 (1989).

Von Hoff, et al., "Phase II evaluation of recombinant γ-interferon in patients with advanced pancreatic carcinoma: A southwest oncology group study" *Journal of Biological Response Modifiers* 9:584-587 (1990).

Walsh, et al., "Phase I study of the combination of alpha-2 interferon and cisplatinum" *Journal of Biological Response Modifiers* 8:11-15 (1989).

Weil-Hillman, et al., "Transient decrease in IL-2 responsive lymphocytes 24 hours after initiation of continuous IL-2 infusion in cancer patients" *Journal of Biological Response Modifiers* 7:424-437 (1988).

Whitehead, et al., "A phase II trial of recombinant tumor necrosis factor in patients with metastatic colorectal adenocarcinoma: A southwest oncology group study" *Journal of Biological Response Modifiers* 9:588-591 (1990).

Yelavarthi, et al., "Analysis of p60 and p80 tumor necrosis factor-alpha" *American Journal of Pathology* 143:1131-1141 (1993).

Zamkoff, et al., "A Phase I trial of subcutaneously administered recombinant tumor necrosis factor to patients with advanced malignancy" *Journal of Biological Response Modifiers* 8:539-552 (1989).

U.S. Appl. No. 09/709,045, filed Nov. 10, 2000, Lentz.

U.S. Appl. No. 09/699,003, filed Oct. 26, 2000, Lentz.

Agishi, Anion-blood contact (ABC reaction) in patients treated by LDL apheresis with dextran sulfate-cellulose column while receiving ACE inhibitors (letter). JAMA; 271:195-6(1994).

Andrews, et al., "Characterization of the receptor for tumor necrosis factor (TNF) and lymphotoxin LT) on human T lymphocytes: TNF and LT differ in their receptor binding properties and the induction of MHC class I proteins on a human CD4+ T cell hybridoma," *J Immunol* 144:2582-2591 (1990).

Banyai et al., "Therapeutic efficiency of lipoprotein(a) reduction by low-density lipoprotein immunoapheresis," *Metabolism* 47(9):1058-1064 (1998).

Bonavida, et al., (eds), Tumor Necrosis Factor/Cachecin and Related Cytokines. Int. Conf. Tumor Necrosis Factor and Related Cytotoxins, Heidelberg, 1987, pp. 7-19 (Karger, Basel1988).

Chen, et al, "Soluble TNF-60 Receptors are constitutively shed and downregulate adhesion molecule expression in malignant gliomas," *J. Neuropathol. Exp. Neural.* 56(5):541-550 (1997).

Clackson, et al., "Making of antibody fragments using phage display libraries," *Nature* 352: 624-688 (1991).

Colman, et al., *Hemostatsis and Thrombosis: Basic Principles and Clinical Practice 2nd. Edition* (Colman, et al., eds.) pp. 242-267 J.B. Lippincott: Philadelphia, PA, 1987.

Cytologic, "Unleash Immunotherapy," Cytologic non CDA info.doc, pp. 1-10 (Apr. 27, 2006).

Daugherty, et al., "Polymerase chain reaction facilitates the cloning, CDR-grafting, and rapid expression of a murine monoclonal antibody directed against the CD18 component of leukocyte integrins," *Nucl. Acids Res.* 19: 2471-2476 (1991).

Ey, et al., "Isolation of pure $IgG_1$, $IgG_{2a}$, and $IgG_{2b}$ immunoglobins from mouse serum using protein A-Sepharose," *Immunochemistry* 15:429-436 (1978).

Feinman, et al., "Tumor necrosis factor is an important mediator of tumor cell killing by human monocytes," *J Immunol* 138:635 (1987).

Gatanaga, et al., "Purification and characterization of an inhibitor (soluble tumor necrosis factor receptor) for tumor necrosis factor and lymphotoxin obtained from the serum ultrafiltrates of human cancer patients," *Proceedings of the National Academy of the USA* 87(22):8781-8784 (1990).

Gatanaga, et al., "Identification of TNF-LT blocking factor(s) in the serum and ultrafiltrates of human cancer patients," *Lymphokine Res* 9:225-9 (1990).

Haranaka, et al, "Cytotoxic activity of tumor necrosis factor (TNF) on human cancer cells in vitro," *Jpn J Exp Med* 51:191 (1981).

Harlow et al, *Antibodies, A Laboratory Manual*, Chapter 13, "Immunoaffinity Purification," pp. 511-552, 1988.

*Hemostasis and Thrombosis: Basic Principles and Clinical Practice* 2nd Ed., Colman, R.W., et al., p. 263 (J.B.Lippincott, Philadelphia, PA 1987).

Hong et al., "Intercellular adhesion molecule-1 expression induced by interleukin (IL)-1 beta or an IL-1 beta fragment is blocked by an IL-1 receptor antagonist and a soluble IL-1 receptor," *Journal of Neuroimmunology*, 44(2):163-170 (1993).

Howard, et al., Vaccinia virus homologues of the *Shope fibroma* virus inverted terminal repeat proteins and a discontinuous ORF related to the tumor necrosis factor receptor family, *Virology* 180(2):633-47 (1991).

IBM Technical Disclosure Bulletin, vol. 19, No. 3. Aug. 1976 pp. 765-768.

Jablonska & Peitruska, "Release of soluble tumor necrosis factor receptors from polymorphonuclear cells of breast cancer patients," *Arch Immunol Ther Exp (Warsz)*. 45(5-6):449-53 (1997).

Kaminska, et al. Clinical significance of serum cytokine measurements in untreated colorectal cancer patients: soluble tumor necrosis factor receptor type I—an independent prognostic factor, *Tumour Biol*. 26(4):186-94(2005).

Kaminska, et al "Pretreatment serum levels of cytokines and cytokine receptors in patients with non-small cell lung cancer, and correlations with clinicopathological features and prognosis. M-CCF—an independent prognostic factor," *Oncology* 70(2):115-25(2006).

Kojima, et al. "Effect of nafamostat mesilate on bradykinin generation during lowdensity lipoprotein apheresis using a dextran sulfate cellulose column," *ASAIO Trans* 37: 644-8(1991).

Lentz, "Continuous whole blood UltraPheresis procedure in patients with metastatic cancer," *Journal of Biological Response Modifiers* 8(5):511-527 (1989).

Lentz, "The role of therapeutic apheresis in the treatment of cancer: a review," *Therapeutic Apheresis* 3(1):40-49 (1999).

Maruyama, et al. "Evidence for aberrant activation of the interleukin-2 autocrine loop by HTLV-1-encoded p40x and T3/Ti complex triggering," *Cell*. 48(2)343-350(1987).

Mathias, et al., "Activation of the Sphingomyelin signaling pathway intact EL4 cells and in a cell-free system by IL-1b," *Science* 259:519-522 (1993).

Matschiner, et al. *Current Advances in Vitamin K Research*, pp. 135-140, John W. Suttie, ed. (Elsevier Science Publishing Co., Inc. 1988).

Mitteregger, et al., "In vitro cell culture systems as the basis for an extracorporeal blood purification strategy in multiorgan failure treatment", *Ther Apher*., 3(3):257-63 (1999).

National Cancer Institute, "Biological Therapies for Cancer: Questions and Answers," National Cancer Institute FactSheet (Aug. 16, 2004).

Old, Antitumor activity of microbial products and tumor necrosis factor, and Bonavida B, et al., (eds): Tumor Necrosis Factor/Cachecin and Related Cytokines, Basell, Karger, p. 7 (1988).

Palaszynski,"Synthetic C-terminal peptide of IL-1 functions as a binding domain as well as an antagonist for the IL-1 receptor," *Biochemical and Biophysical Research Communications*, 147(1):204-211(1987).

Pennica et al., "Characterization of a recombinant extracellular domain of the type 1 tumor necrosis factor receptor: evidence for tumor necrosis factor-alpha induced receptor aggregationm," *Biochemistry* 31(4):1134-1141(1992).

Pennica et al.," Biochemical characterization of the extracellular domain of the 75-kilodalton tumor necrosis factor receptor," *Biochemistry* 32(12): 3131-3138(1993).

Philip & Epstein, "Tumor necrosis factor as immunomodulator and mediator of monocyte cytotoxicity induced by itself, Gamma-interferon and Interleukin-1," *Nature* 323(6083):86-87 (1986).

Product description: catalog No. AB-225-PB catalog of R&D Systems. (1994).

Product description: catalog No. AB-226-PB catalog of R&D Systems (1994).

Product description: catalog Nos. FAB225F catalog of R&D Systems (1998).

Product description: catalog Nos. MAB225 catalog of R&D Systems (1998).,

Product description: catalog Nos. AF-425-PB catalog of R&D Systems (1998).

Selinsky, et al., "Multifaceted inhibition of anti-tumor immune mechanisms by soluble tumour necrosis factor receptor type-1," *Immunology* 94(1):88-93 (1998).

Shibata, et al., "Changes of cell-mediated immunity with an advance of cancer-relation to the th1/th2 balance and inhibitors of th1 cytokines", *Biotherapy*, 12(5):715-17 (1998).

Tetta, et al., "Continuous plasma filtration coupled with sorbents," *Kidney International* 53(66):S186-S189 (1998).

Urban, et al., "Tumor necrosis factor: A potent effector molecule for tumor cell killing by activated macrophages," *Proc Natl Acad Sce USA* 83:5233-37 (1986).

Van Zee, et al., "Tumor necrosis factor soluble receptors circulate during experimental and clinical inflammation and can protect against excessive tumor necrosis factor alpha in vitro and in vivo" *PNAS* 89:4845-4849 (1992).

Verma et al., "Antibody engineering: comparison of bacterial, yeast, insect and mammalian expression systems," *Journal of Immunological Methods*, 216(1-2):165-181(1998).

Warzocha, et al. "Tumor necrosis factor ligand-receptor system can predict treatment outcome in lymphoma patients," *J Clin Oncol*. 15(2):499-508(1997).

Winter, et al. "Synthetic human antibodies and a strategy for protein engineering," *FEBS Letters*, 430:92-94(1998).

Yamazaki et al. Biocompatibility of plasma separator of an improved cellulose acetate hollow fiber. In: Sieberth HG (ed). Plasma Exchange. New York: fk Schattauer, 45-51(1980).

Ziegler-Heitbrock, et al., "Tumor necrosis factor as effector molecule in monocyte-mediated cytotoxicity," *Cancer Res* 46:5947-52 (1986).

Holohan, et al. "Regression of canine mammary carcinoma after immunoadsorption therapy," *Cancer Res*. 42(9):3663-8(1982).

Lentz, et al. "Low Molecular weight Protein Apheresis and Regression of Breast Cancer", *Abstract in Japanese Society of Apheresis* 15 Supplement S31, W4-3(1996).

Suzuki, "A prospect of anti-cytokine therapy,", Igiku no Ayurni, Japan, Ishiyaku Publishers, Inc., 167(5)432-435 (1993).

Olsson, "Isolation and characterization of a tumor necrosis factor binding protein from urine", *Eur. J. Haematol*., 42(3):270-275 (1989).

Peetre, "A tumor necrosis factor binding protein is present in human biological fluids", *Eur, J. Haematol*., 41(3)414-419 (1988).

Dummer, "Circulating interleukin-2 receptors are a group of multimeric proteins with immunoreactivity for interleukin-2 receptor alpha, beta, and gamma chains", *J. interferon Cytokine Res*., 16(4):315-320 (1996).

K.A. Fitzgerald, et al., Cytokine Facts Book Second Edition, Academic Press New York, pp. 71 and 272 (2001).

Lotem, et al., "Hematopoietic cytokines inhibit apoptosis induced by transforming growth factor beta 1 and cancer chemotherapy compounds in myeloid leukemic cells", *Blood*, 80(7):1750-1757 (1992).

Novick, "Soluble cytokine receptors are present in normal human urine", *J. Exp. Med*., 170(4):1409-1414 (1989).

Young, et al., "Increased recurrence and metastasis in patients whose primary head and neck squamous cell carcinomas secreted granulocyte-macrophage colony-stimulating factor and contained CD34+ natural suppressor cells", *International J. Cancer*, 74(1):69-74 (1997).

Rivas, et al., "Expression of granulocyte-macrophage colony-stimulating factor receptors in human prostate cancer", *Blood*, 91:1037-47 (1998).

Adolf and Frühbeis, "Monoclonal antibodies to soluble human TNF receptor (TNF binding protein) enhance its ability to block TNF toxicity.", *Cytokine*, 4(3):180-184 (1992).

Bjornberg, et al., "Mechanisms involved in the processing of the p55 and the p75 tumor necrosis factor (TNF) receptors to soluble receptor forms", *Lymphokine Cytokine Res*., 13(3):203-11 (1994).

Csehi, et al., "Tumor necrosis factor (TNF) interferes with insulin signaling through the p55 TNF receptor death domain", *Biochem Biophys Res Commun*, 329(1):397-405 (2005).

Feng, "Regulatory roles and molecular signaling of TNF family members in osteoclasts", *Gene*, 350(1):1-13 (2005).

Gadducci, et al., "Serum levels of tumor necrosis factor (TNF), soluble receptors for TNF (55- and 75-kDa sTNFr), and soluble CD14 (sCD14) in epithelial ovarian cancer", *Gynecol Oncol*, 58(2):184-8 (1995).

Grell, et al., "The type 1 receptor (CD120a) is the high-affinity receptor for soluble tumor necrosis factor", *Proc Natl Acad Sci U S A.*, 95(2):570-5 (1998).

Grosen, et al, "Measurement of the soluble membrane receptors for tumor necrosis factor and lymphotoxin in the sera of patients with gynecologic malignancy", *Gynecol Oncol*, 50(1):68-77 (1993).

Hasegawa, et al., "Increased soluble tumor necrosis factor receptor levels in the serum of elderly people", *Gerontology*, 46(4):185-8 (2000).

Holtmann, et al., "The emerging distinct role of TNF-receptor 2 (p80) signaling in chronic inflammatory disorders", *Arch immunol Ther Exp (Warsz)*, 50(4):279-88 (2002).

Jablonska, et al., "Tumor necrosis factor-alpha and soluble tumor necrosis factor receptors in the culture supernatants of polymorphonuclear cells and peripheral blood mononuclear cells from cancer patients", *Eur Cytokine Netw*, 9(2):155-9 (1998).

Liu, et al, "Molecular mechanism of TNF signaling and beyond", *Cell Res3*, 15(1):24-7 (2005).

Macallan, et at, "Development of a novel TNF alpha ligand-receptor binding assay for screening NATCHEM Libraries", *J Recept Signal Transduct Res*, 17(1-3):521-9 (1997).

Maier, et al., "Physiological levels of pro- and anti-inflammatory mediators in cerebrospinal fluid and plasma: a normative study", *J Neurotrauma*, 22(7):822-35 (2005).

Muc-Wierzgon, et al., "Circadian fluctuations of melatonin, tumor necrosis factor-alpha and its soluble receptors in the circulation of patients with advanced gastrointestinal cancer", *J Exp Clin Cancer Res*, 22(2):171-8 (2003).

Nophar, et al., "Soluble forms of tumor necrosis factor receptors (TNF-Rs). The cDNA for the type I TNF-R, cloned using amino acid sequence data of its soluble form, encodes both the cell surface and a soluble form of the receptor", *EMBO J*, 9(10):3269-78 (1990).

Onsrud, et al., "Comparison between soluble tumor necrosis factor receptors and CA125 in peritoneal fluids as a marker for epithelial ovarian cancer", *Gynecol Oncol*, 57(2):183-7 (1995).

Onsrud, et al., "Soluble tumor necrosis factor receptors and CA 125 in serum as markers for epithelial ovarian cancer", *Tumour Biol*, 17(2):90-6 (1996).

Rzymski, et at, "Serum tumor necrosis factor alpha receptors p55/p75 ratio and ovarian cancer detection", *J Gynaecol Obstet*, 88(3):292-8 (2005).

Serwin, et at, "[Soluble tumor-necrosis-factor-alpha receptor type-1 as a marker of activity of psoriasis vulgaris and effects of its treatment]", *Przegl Lek*, 62(2):95-7 (2005).

Serwin, at al., "Soluble tumor necrosis factor alpha receptor type 1 in psoriasis patients treated with narrowband ultraviolet B" *Photodermatol Photoimmunol Photomed*, 21(4):210-1 (2005).

Shai, et at, "A prospective study of soluble tumor necrosis factor-alpha receptor 11 (sTNF-RII) and risk of coronary heart disease among women with type 2 diabetes", *Diabetes Care*, 28(6):1376-82 (2005).

Sukhikh, et al., "Disorders in cytokine gene expression in endometrial hyperplasia and effect of hormone therapy", *Bull Exp Biol Med.*, 139(2):235-7 (2005).

Tesarova, et al., "Soluble TNF and IL-2 receptors in patients with breast cancer", *Med Sci Monit*, 6(4):661-7 (2000).

Theiss, et al., "Tumor Necrosis Factor (TNF) {alpha} Increases Collagen Accumulation and Proliferation in Intestinal Myofibroblasts via TNF Receptor 2", *J Biol Chem*, 280(43):36099-109 (2005).

Wajant, et al., "Tumor necrosis factor signaling", *Cell Death Differ*, 10(11:45-65 (2003).

Wozel, "[Etanercept an effective TNF alpha-antagonist in the treatment of psoriatic arthritis and chronic plaque psoriasis,]" *Hautarzt*, 56(9):819-830 (2005).

Jablonska & Peitruska, "Release of soluble tumor necrosis factor receptors from polymorphoniclear cells of breast cancer parients," *Arch. Immunol. Ther. Exp. (Warsz)* 45(5-6)449-453 (1997).

Kabat, et al., *Sequences of Proteins of Immunological Interest* 4$^{th}$ Ed. (U.S. Dept. Health and Human Services, Bethesda, MD, 1987).

Langkopf, et al., "Soluble tumor necrosis factor receptors as prognostic factors in cancer patients," *Lancet* 344:57-58 (1994).

Mathias, et al., "Activation of the Sphingomyelin signaling pathway intact EL4 cells and in a cell-free system by IL-Ib," *Science* 259:519-522 (1993).

Matschiner, et al., *Current Advances in Vitamin K Research*, pp. 135-140, John W. Suttie, ed. (Elsevier Science Publishing Co., Inc. 1988).

Old, Antitumor activity of microbial products and tumor necrosis factor, and Bonavida B, et al., (eds): Tumor Necrosis Factor/Cachecin and related Cytokines, Basell, Karger, p7 (1988).

Philip, et al., "Tumor necrosis factor as immunomodulator and mediator of monocyte cytotoxicity induced by itself, Gamma-interferon and Interleukin-1," *Nature* 323:86 (1986).

Urban, et al., "Tumor necrosis factor: A potent effector molecule for tumor cell killing by activated macrophages," *Proc Natl Acad Sce USA* 83:5233 (1986).

Ziegler-Heitbrock, et al., "Tumor necrosis factor as effector molecule in monocyte-mediated cytotoxicity," *Cancer Res* 46:5947 (1986).

U.S. Appl. No. 12/685,307, Lentz.

Ammirati et al., "Detection of TNF inhibitors (soluble receptors) in the sera and tumor cyst fluid of patients with malignant astrocytomas of the brain" Front Biosci Oct. 1;6:B17-24 (2001).

Burger et al., "Association between serum levels of soluble tumor necrosis factor receptors/CA 125 and disease progression in patients with epithelial ovarian malignancy: a gynecologic oncology group study" Cancer 101(1):106-15 (2004).

Chen et al., "Experimental vaccine strategies for cancer immunotherapy" J Biomed Sci 5(4):231-52 (1998).

Csehi et al. "Tumor necrosis factor (TNF) interferes with insulin signaling through the p55 TNF receptor death domain." Biochem Biophys Res Commun. Apr. 1, 2005;329(1):397-405.

Eisen, "General Immunology", J.B. Lippincott Company, 78 (1980).

Feng, "Regulatory roles and molecular signaling of TNF family members in osteoclasts." Gene. Apr. 25, 2005;350(1):1-13.

Gonzalez et al., "A novel cancer vaccine composed of human-recombinant epidermal growth factor linked to a carrier protein: report of a pilot clinical trial" Ann Oncol 9(4):431-5 (1998).

Holtmann et al. "The emerging distinct role of TNF-receptor 2 (p80) signaling in chronic inflammatory disorders." Arch Immunol Ther Exp (Warsz). 2002;50(4):279-88.

Kircheis et al., "Cytokine gene-modified tumor cells for prophylactic and therapeutic vaccination: IL-2, IFN-gamma, or combination IL-2 + IFN-gamma" Cytokines Cell Moll Ther 4(2)2:95-103 (1998).

"Laboratory Filtration Concepts," Pall Life Sciences, http://www.pall/com/catalogs/filterbook/concepts.asp, retrieved Apr. 12, 2002.

Liu et al. "Molecular mechanism of TNF signaling and beyond." Cell Res. Jan. 2005;15(1):24-7.

Mack et al., "Five-year results of a phase II study with low-dose bacille Calmette-Guerin therapy in high-risk superficial bladder cancer" Urology 45(6):958-61 (1995).

Maier et al., "Physiological levels of pro- and anti-inflammatory mediators in cerebrospinal fluid and plasma: a normative study" J Neurotrauma 22(7):822-35 (2005).

Moller et al., "Vaccination with IL-7 gene-modified autologous melanoma cells can enhance the anti-melanoma lytic activity in peripheral blood of patients with a good clinical performance status: a clinical phase I study" Br J Cancer 77(11):1907-16 (1998).

Mordoh et al. "Allogeneic cells vaccine increases disease-free survival in stage III melanoma patients. A non randomized phase II study" Medicina (B Aires) 57(4)4:421-7 (1997).

Moviglia "Development of tumor B-cell lymphocyte hybridoma (TBH) autovaccination. Results of phase I-II clinical trial" Transfus Sci 17(4):643-9 (1996).

Muc-Wierzgon et al. "Circadian fluctuations of melatonin, tumor necrosis factor-alpha and its soluble receptors in the circulation of patients with advanced gastrointestinal cancer" J Exp Clin Cancer Res. Jun. 2003;22(2):1 71-8.

Rzymski et al. "Serum tumor necrosis factor alpha receptors p55/p75 ratio and ovarian cancer detection." Int J Gynaecol Obstet. Mar. 2005;88(3):292-8.

Sasaki et al., "Identification of a soluble GM-CSF binding protein in the supernatant of a human choriocarcinoma cell line," Biochem. Biophys. Res. Commun. 183(1):252-257 (1992). (Abstract Only).

Serwin et al. "[Soluble tumor-necrosis-factor-alpha receptor type-1 as a marker of activity of psoriasis vulgaris and effects of its treatment]" Przegl Lek. 2005;62(2):95-7.

Serwin et al. "Soluble tumor necrosis factor alpha receptor type 1 in psoriasis patients treated with narrowband ultraviolet B" Photodermatol Photoimmunol Photomed. Aug. 2005;21(4):210-1.

Shai et al. "A prospective study of soluble tumor necrosis factor-alpha receptor II (sTNF-RII) and risk of coronary heart disease among women with type 2 diabetes." Diabetes Care. Jun. 2005;28(6):1376-82.

Sinclair, "Filtration Fundamentals: Is Knowledge of Filter Technology Something You Let Fall Through the Cracks?" The Scientist 12[19]:18 (1998), www.the-scientist.com/yr1998/sept/profile1_980928.html, retrieved on Apr. 12, 2002.

Sivanandham et al., "Colon cancer cell vaccine prepared with replication-deficient vaccinia viruses encoding B7.1 and interleukin-2 induce antitumor response in syngeneic mice" Cancer Immunol Immunother 46(5):261-7 (1998).

Sukhikh et al. "Disorders in cytokine gene expression in endometrial hyperplasia and effect of hormone therapy." Bull Exp Biol Med. Feb. 2005;139(2):235-7.

Talwar "Vaccines for control of fertility and hormome-dependent cancers" Immunol Cell Biol 75(2):184-9 (1997).

Thiess et al. "Tumor necrosis factor (TNF) alpha increases collagen accumulation and proliferation in intestinal myofibroblasts via TNF receptor 2." J Biol Chem. Oct. 28, 2005;280(43):36099-109. Epub Sep. 1, 2005.

Wajant et al. "Tumor necrosis factor signaling." Cell Death Differ. Jan. 2003;10(1):45-65.

Wozel "Etanercept. An effective TNF alpha-antagonist in the treatment of psoriatic arthritis and chronic plaque psoriasis" Hautarzt. Sep. 2005;56(9):819-30.

* cited by examiner

METHOD AND SYSTEM TO REMOVE CYTOKINE INHIBITOR IN PATIENTS

This application is a continuation in part of U.S. Ser. No. 09/699,003 filed Oct. 26, 2000 now U.S. Pat. No. 7,854,717, which is a continuation of U.S. Ser. No. 09/316,226 filed May 21, 1999, now U.S. Pat. No. 6,231,536, which is a continuation in part of U.S. Ser. No. 09/083,307 filed May 22, 1998, issued as U.S. Pat. No. 6,620,382, which claims priority under 35 U.S.C. 119 to U.S. Ser. No. 60/164,695 filed Nov. 10, 1999.

This application claims priority to U.S. Ser. No. 60/164,695, filed Nov. 10, 1999.

BACKGROUND OF THE INVENTION

The present invention is generally in the field of enhancing an immune response, and particularly relates to the removal of TNF inhibitors in a patient, such as a cancer patient, to promote inflammation and thereby induce remission of the cancer.

Conventional cancer therapy is based on the use of drugs and/or radiation which kills replicating cells, hopefully faster than the agents kill the patient's normal cells. Surgery is used to reduce tumor bulk, but has little impact once the cancer has metastasized. Radiation is effective only in a localized area.

The treatments can in themselves kill the patient, in the absence of maintenance therapy. For example, for some types of cancer, bone marrow transplants have been used to maintain the patient following treatment with otherwise fatal amounts of chemotherapy. Efficacy has not been proven for treatment of solid tumors, however. "Cocktails" of different chemotherapeutic agents and combinations of very high doses of chemotherapy with restorative agents, for example, granulocyte macrophage colony stimulating factor ("GM-CSF"), erythropoietin, thrombopoetin granulocyte stimulating factor, ("G-CSF"), macrophage colony stimulating factor ("M-CSF") and stem cell factor ("SCF") to restore platelet and white cell levels, have been used to treat aggressive cancers. Even with the supportive or restrictive therapy, side effects are severe.

Other treatments have been tried in an attempt to improve mortality and morbidity. Vaccines to stimulate the patient's immune system have been attempted, but not with great success. Various cytokines, alone or in combination, such as tumor necrosis factor, interferon gamma, and interleukin-2 ("IL-2") have been used to kill cancers, but have not produced cures. More recently, anti-angiogenic compounds such as thalidomide have been tried in compassionate use cases and shown to cause tumor remission. In animal studies, compounds inducing a procoagulant state, such as an inhibitor of protein C, have been used to cause tumor remission. New studies have shown that soluble cytokine receptors, such as tumor necrosis factor receptors ("TNF-Rs") which are released in a soluble form from tumor cells, in high concentrations relative to normal cells, may restore the immune system's attack on the tumor cells (Jablonska and Peitruska, Arch. Immunol. Ther. Exp. (Warsz) 1997, 45(5-6), 449-453; Chen, et al., J. Neuropathol. Exp. Neurol. 1997, 56(5), 541-550).

U.S. Pat. No. 4,708,713 to Lentz describes an alternative method for treating cancer, involving ultrapheresis to remove compounds based on molecular weight, which promotes an immune attack on the tumors by the patient's own white cells.

Despite all of these efforts, many patients die from cancer; others are terribly mutilated. It is unlikely that any one therapy will be effective to cure all types of cancer.

It is therefore an object of the present invention to provide a method and system for treatment of solid tumors.

It is a further object of the present invention to provide a method and compositions that does not involve non-selective, extremely toxic, systemic chemotherapy.

SUMMARY OF THE INVENTION

A method to treat disorders characterized by production of soluble TNF receptors, such as many types of cancer, and certain diseases such as HIV, where the disease immunosuppresses the patient, has been developed. Antibodies which bind to TNF receptor, including the soluble TNF receptor, are administered to the patient in an amount effective to neutralize the molecules which block binding of TNF to the receptor, thereby inducing inflammation. In the preferred embodiment, the patient's blood is passed through a column having antibodies immobilized thereon, which bind to and remove the soluble TNF receptor molecules. The process can be performed alone or in combination with other therapies, including radiation, chemotherapy (local or systemic, for example, treatments using alkylating agents, doxyrubicin, carboplatinum, cisplatinum, and taxol, and other drugs which may be synergistic in effect with "unblocked" cytokines: or anti-angiogenic factors. Antibodies may be utilized which are immunoreactive with one or more of the following: tumor necrosis factor receptor-1 ("TNFR-1"), tumor necrosis factor receptor-2 ("TNFR-2"), interleukin-2 receptor ("IL-2R"), interleukin-1 receptor ("IL-1R"), interleukin-6 receptor ("IL-6R"), or interferon-gamma receptor ("sIFN-gammaR"). The patient is preferably treated daily for at least three weeks, diagnostic tests conducted to verify that there has been shrinkage of the tumors, then the treatment regime is repeated as needed.

DETAILED DESCRIPTION OF THE INVENTION

Innate, natural and antigen specific killer mechanisms represent the best arsenal for dealing with melanoma cells in vitro and in vivo. Central to these cellular destructive mechanisms is tumor necrosis factor (TNF-), an inflammatory cytokine produced by macrophages and earlier mononuclear cells and TNF-, a related cytokine produced and secreted by killer T-lymphocytes with highly selective antigen specific receptors, Old L. J., Antitumor activity of microbial products and tumor necrosis factor, and Bonavida B, et al., (eds): Tumor Necrosis Factor/Cachecin and Related Cytokines, Basell, Karger, 1988. p 7; Haranaka K., et al, Cytotoxic activity of tumor necrosis factor (TNF) on human cancer cells in vitro, *Jpn J Exp Med* 1981; 51:191; Urban J. L. II, et al., Tumor necrosis factor: A potent effector molecule for tumor cell killing by activated macrophages, *Proc Natl Acad Sce USA* 1986; 83-5233; Philip R., et al., Tumor necrosis factor as immunomodulator and mediator of monocyte cytotoxicity induced by itself, Gamma-interferon and Interleukin-1, *Nature* 1986; 323:86; Ziegler-Heitbrock H. W., et al., Tumor necrosis factor as effector molecule in monocyte-mediated cytotoxicity, *Cancer Res* 1986; 46:5947; and Feinman R., et al., Tumor necrosis factor is a important mediator of tumor cell killing by human monocytes, *J Immunol* 1987; 138:635. They derive from billions of clones, each with its own specificity. Thus, one clone of these thymus derived lymphocytes gives rise to T-killer (cytotoxic lymphocytes), or other functional classes each with the one specificity of the parent clone. Their mechanisms are related to both antibody dependent and antibody independent cellular tumor toxicity. Receptors for TNF on neoplastic, viral infected, aged cells or those otherwise targeted for destruction can be both a blessing and a curse. In a positive role, they allow binding of TNF to the surface for internalization and destruction of the cell. Unfortunately this receptor hypothesis has a double edge. Certain neoplastic cells such as active melanomas secrete large amounts of these receptors (sTNF-R1 and sTNF-R2) that promptly bind TNF before it can get within the vicinity of the cell, Haranaka K., et al, Cytotoxic activity of tumor necrosis factor (TNF) on human cancer cells in vitro, *Jpn J Exp Med* 1981; 51:191; Urban J. L. II, et al., Tumor necrosis factor: A potent effector molecule for tumor cell killing by activated macrophages, *Proc Natl Acad Sce USA* 1986; 83-5233; Philip R., et al., Tumor necrosis factor as immunomodulator and mediator of monocyte cytotoxicity induced by itself, Gamma-interferon and Interleukin-1, *Nature* 1986; 323:86; Ziegler-Heitbrock H. W., et al., Tumor necrosis factor as effector molecule in monocyte-mediated cytotoxicity, *Cancer Res* 1986; 46:5947; and Feinman R., et al., Tumor necrosis factor is a important mediator of tumor cell killing by human monocytes, *J Immunol* 1987; 138:635. This serves as a defense mechanism on the part of the targeted cell rendering the host immune system ineffective. TNF-R1 and R2 have been characterized with respect to molecular weights (55 and 75 kD respectively), Old L. J., Antitumor activity of microbial products and tumor necrosis factor, and Bonavida B, et al., (eds): Tumor Necrosis Factor/Cachecin and Related Cytokines, Basell, Karger, 1988. p 7, Langkopf F., et al., Soluble tumor necrosis factor receptors as prognostic factors in cancer patients, *Lancet* 1994; 344:57-58; Howard S. T., et al., Vaccinia virus homologues of the Shope fibroma virus inverted terminal repeat proteins and a discontinuous ORF related to the tumor necrosis factor receptor family, *Virology* 1991; 180:633-664; Mathias S, et al., Activation of the Sphingomyelin signaling pathway intact EL4 cells and in a cell-free system by IL-1b, *Science* 1993; 259-519-522; and Andrews J. S., et al., Characterization of the receptor for tumor necrosis factor (TNF) and lymphotoxin LT) on human T lymphocytes: TNF and LT differ in their receptor binding properties and the induction of MHC class I proteins on a human CD4+ T cell hybridoma, *J Immunol* 1990; 144:2582-2591. They serve to both down regulate the immune response in a normal fashion and overly suppress the immune response as stated above with respect to certain malignancies. They are particularly abundant, and at high level, in patients with melanoma.

I. ANTI-CYTOKINE RECEPTOR MOLECULES

Selective removal or neutralization of the soluble cytokine receptors (which function as inhibitors of the cytokine) can be used to promote a selective, safe inflammatory response against a tumor or cells infected with a pathogen such as a virus like HIV or parasite. The neutralizing agent is typically an antibody reactive with the receptor, the antibodies will typically be reactive with both the soluble and immobilized forms of the receptor. These include soluble tumor necrosis factor receptor ("sRNF-R"), soluble interleukin-2 receptor ("sIL-2R"), soluble interleukin-1 receptor ("sIL-1R"), soluble interleukin-6 receptor ("sIL-6R"), or soluble interferon-gamma receptor ("sIFN-gammaR"). The advantage of selective removal or neutralization is that the same beneficial effect is obtained in treatment of the disorder but the treatment is much less expensive and safer since exogenous plasma or albumin does not have to be administered to the patient when there is selective removal, as in the case of ultrapheresis and the cytotoxic effects of radiation and chemotherapy are avoided.

The receptors can be removed by binding to the cytokine, an epitope thereof, or an antibody to the receptor. The antibodies to the receptors can be immobilized in a filter, in a column, or using other standard techniques for binding reactions to remove proteins from the blood or plasma of a patient, or administered directly to the patient in a suitable pharmaceutically acceptable carrier such as saline. As used herein, antibody refers to antibody, or antibody fragments (single chain, recombinant, or humanized), immunoreactive against the receptor molecules. In the most preferred embodiment, the antibody is reactive with the carboxy-terminus of the shed receptor molecules, thereby avoid concerns with signal transduction by the receptor is still present on the cell surface.

Antibodies can be obtained from various commercial sources such as Genzyme Pharmaceuticals. These are preferably humanized for direct administration to a human, but may be of animal origin if immobilized in an extracorporeal device. Antibodies may be monoclonal or polyclonal. The antibodies and device should be sterilized and treated to remove endotoxin and other materials not acceptable for administration to a patient.

Antibodies to the receptor proteins can be generated by standard techniques, using human receptor proteins. Antibodies are typically generated by immunization of an animal using an adjuvant such as Freund's adjuvant in combination with an immunogenic amount of the protein administered over a period of weeks in two to three week intervals, then isolated from the serum, or used to make hybridomas which express the antibodies in culture. Because the methods for immunizing animals yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarily-determining hypervariable regions (CDRs) are of non-human origin, whereas all framework regions (FR) of variable domains are products of human genes. These "humanized" antibodies present a lesser xenographic rejection stimulus when introduced to a human recipient.

To accomplish humanization of a selected mouse monoclonal antibody, the CDR grafting method described by Daugherty, et al., (1991) *Nucl. Acids Res.*, 19:2471-2476, incorporated herein by reference, may be used. Briefly, the variable region DNA of a selected animal recombinant anti-idiotypic ScFv is sequenced by the method of Clackson, T., et al., (1991) *Nature*, 352:624-688, incorporated herein by reference. Using this sequence, animal CDRs are distinguished from animal framework regions (FR) based on locations of the CDRs in known sequences of animal variable genes. Kabat, H. A., et al., Sequences of Proteins of Immunological Interest, $4^{th}$ Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grated DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generated a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generated a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

The antibodies can be formulated in standard pharmaceutical carriers for administration to patients in need thereof. These include saline, phosphate buffered saline, and other aqueous carriers, and liposomes, polymeric microspheres and other controlled release deliver devices, as are well known in the art. The antibodies can also be administered with adjuvant, such as muramyl dipeptide or other materials approved for use in humans (Freund's adjuvant can be used for administration of antibody to animals).

In the preferred embodiment, antibodies are immobilized to a solid support, such as the SEPHAROSE™ column in the examples, using standard techniques such as cyanogen bromide or commercially available kits for coupling of proteins to membranes formed of materials such as nitrocellulose or polycarbonate.

Treatment is conducted over a period of time until a positive indication is observed. This is typically based on diagnostic tests which show that there has been some reduction in tumor size or which suggests tumor inflammation. The patient is preferably treated daily for three weeks, diagnostic tests conducted to verity that there has been shrinkage of the tumors and/or inflammation, then the treatment regime is repeated.

Surgical (or vacuum) removal of necrotic material may be required prior to or during treatment to avoid toxicity associated with high tumor burden.

II. TREATMENT WITH ADJUVANT THERAPIES

It would clearly be advantageous to cause complete remissions. Based on the presumed mechanism that the process is removing immune inhibitors produced by the tumors, especially inhibitors of cytokines and other immune mediators, it is possible to treat the patients with adjuvant or combination therapies, that enhance the results achieved with the ant61bodies to TNF receptors. These include anti-angiogenic compounds, such as thalidomide, procoagulant compounds, cytokines and other immunostimulants. Standard chemotherapeutic agents and/or radiation can also be used with the ultrapheresis with the antibody treatment.

A. Anti-Angiogenic Compounds

Any anti-angiogenic compound can be used. Exemplary anti-angiogenic compounds include O-substituted fumagillol and derivatives thereof, such as TNP-470, described in U.S. Pat. Nos. 5,135,919, 5,698,586, and 5,290,807 to Kishimoto, et al.; angiostatin and endostatin, described in U.S. Pat. No. 5,290,807, 5,639,725 and 5,733,876 to O'Reilly; thalidomide, as described in U.S. Pat. Nos. 5,629,327 and 5,712,291 to D'Amato; and other compounds, such as the anti-invasive factor, retinoic acid, and paclitaxel, described in U.S. Pat. No. 5,716,981 to Hunter, et al., and the metalloproteinase inhibitors described in U.S. Pat. No. 5,713,491 to Murphy, et al. Thalidomide is administered once daily, 200 mg orally.

B. Procoagulant Compounds

Protein C is a vitamin K-dependent plasma protein zymogen to a serine protease. Upon activation it becomes a potent anticoagulant. Activated protein C acts through the specific proteolysis of the procoagulant cofactors, factor VIIIa and factor Va. This activity requires the presence of another vitamin K-dependent protein, protein S, calcium and a phospholipid (presumably cellular) surface. As described in *Hemostasis and Thrombosis: Basic Principles and Clinical Practice* 2nd Ed., Colman, R. W., et al., p. 263 (J. B. Lippincott, Philadelphia, Pa. 1987), protein C circulates in a two-chain form, with the larger, heavy chain bound to the smaller light chain through a single disulfide link. Protein C is activated to activated protein C (APC). Thrombin is capable of activating protein C by the specific cleavage of the $Arg^{12}$-$Leu^{13}$ bond in the heavy chain. In vivo, in the presence of physiological concentrations of calcium, the rate of this activation is enhanced dramatically when thrombin is bound to the endothelial cell cofactor, thrombomodulin. Matschiner, et al., *Current Advances in Vitamin K Research*, pp. 135-140, John W. Suttie, ed. (Elsevier Science Publishing Co., Inc. 1988) have further reviewed the role of the Vitamin K dependent proteins in coagulation.

Blockage of the natural anticoagulant pathways, in particular the protein C pathway, uses the natural procoagulant properties of the tumor to target the tumor capillaries for microvascular thrombosis, leading to hemorrhagic necrosis of the tumor, as described in U.S. Pat. No. 5,147,638 to Esmon, et al. Examples of such compounds include anti-protein C and anti-protein S.

C. Cytokines

The biologic activity and clinical effectiveness of pro-inflammatory cytokines is augmented by ultrapheresis in the patient with cancer and other states of acquired immune tolerance Specifically, both TNF alpha and TNF beta, in doses of between approximately 100 to 500 micrograms per meter squared body surface area (M2BSA), can enhance the immune reaction in aggressive tumors. Monocyte and lymphocyte activation is augmented by INF-alpha, INF-beta and gamma. The IL-1 and IL-2 receptor antagonists are removed by ultrapheresis and thereby upregulate the in vivo activity of these cytokines. An 80 kD glycoprotein, which is responsible for inhibiting blastoid transformation in advanced malignancy, chronic infectious disease and pregnancy, has recently been found, and appears to be responsible for the loss of delayed hypersensitivity reactions in these diseases, which is removed by this process. This is significant because in removing this type of suppression, vaccines of all types will work better. Dosage regimes for IFN-alpha and beta are 3 M units subcutaneous three times a week up to 20 M units/M2 BSA daily. Interferon-gamma is administered in a dosage of between 100 to 1000 micgms per day.

D. Chemotherapeutic Agents

Preferred chemotherapeutic agents are those which are synergistic with TNF, for example, alkylating agents, doxyrubicin, carboplatinum, cisplatinum, and tomoxifen. Tamoxifen plays a role not only in blocking of estrogen receptors but also certain growth factor receptors such as epidermal derived growth factor ("EDGF"), fibroblast derived growth factor ("FDGF"), tumor derived growth factor ("TDGF"), TDGF-β and platelet derived growth factor ("PDGF") and therefore may be complementary to inflammation against cancers provoked by ultrapheresis.

E. Radiation

Radiation therapy is destructive of normal tissue, causing tumors to die partially by an inflammatory attack. Ultrapheresis allows the use of lower doses of radiation to kill residual tumor cells and spare normal tissue. In a preferred method, ultrapheresis is used as the initial therapy, followed by radiation at approximately one-half of the normal dosages. It is well established that TNF kills tumor cells by generating free oxygen radicals, hydroxyl radicals and halide ions, and that radiation therapy generates carbonium ions in tissue. Therefore the combination of the two is more effective in killing cancer cells than either alone.

III. EXAMPLES

Example 1

Treatment of a Patient with Ultrapheresis Having Antibodies Immobilized on the Filter Materials and Methods Monoclonal antibody was obtained from R&D Systems, Minneapolis, Minn., and purified for administration to a patient. This antibody is reactive with TNF R1 and R2 inhibitors.

A filtration system was assembled using an Eva Flux 4 A filter as the primary filter to remove ultrafiltrate containing these inhibitors from the cancer patient's blood. Monoclonal antibody in a dose of 1 mg per liter of normal ultrafiltrate of the monoclonal antibody and 1 mg of the $2 monoclonal antibody were added to that replacement solution. In this circuit the ultrafiltrate of the initial 4 A filter was delivered by a separate blood pump to a Kuraray 3 A filter. The retentate of the 3A filter was then discarded and the ultrafiltrate of the 3A filter was metered back into the filtered blood from the 4 A filter as replacement solution. To make the discard; i.e., the retentate of the 3 A filter, normal ultrafiltrate with monoclonal antibody added to it was metered into the intra circuit between the 4 A and 3 A filters.

Results

Addition of the monoclonal antibodies to ultrafiltrated cancer sera that possess elevated levels of the inhibitors decreases the level of detectable inhibitor by Elias Assay to zero.

Addition of the monoclonal antibodies to the replacement fluid following ultrapheresis led to an increased reduction of both the soluble receptor to TNF R1 and R2 in the ultrafiltrate of the second filter.

The purpose of this was to test whether or not this murine monoclonal antibody could capture the inhibitor and aid in its removal from blood since the complex of antibody and antigen could not pass through the pores of the 3 A filter and thus be discarded in the retentate of the 3A filter. This was considerably more effective than the single separation technique and replacement with normal ultrafiltrate. There was also a heightened tumor specific inflammatory response by doing this and an increased rate of tumor destruction. These experiments strongly indicate that the monoclonal antibody, preferably humanized to 97% to 99% human form by substituting human constant regions for human constant regions on the antibody, preserve its capturing and neutralizing capability with the murine variable regions of the antibody and use the antibody as the therapeutic drug in clinical trials with a very high expectation that it would neutralize soluble receptors to TNF and cause tumor destruction in a human.

Example 2

Treatment of a Patient with mAb to TNF Receptors

A patient with vaginal metastasis of colon cancer was treated for one week with a three hour infusion of monoclonal antibody to TNF receptor 1 and TNF receptor 2. This led to a 75% reduction in the tumor size within one week.

Example 3

Treatment of Melanoma Patient

A procedure is described in case report form, that utilizes apheresis and immunological affinity chromatography to treat a melanoma patient with short term need and weakening long term prognosis.

Previous studies utilizing ultrafiltration, with selective pore sieving by passing patient's plasma through cartridges, have been shown to reduce sTNF-R1 and R2 levels. The period of this procedure seems to be of sufficient length to allow TNF to rebound and selectively produce apoptosis or membrane disarray of melanoma cells, Gatanaga T., et al., Identification of TNF-LT blocking factor(s) in the serum and ultrafiltrates of human cancer patients, *Lymphokine Res* 1990; 9:225-9. Instead of using ultrafiltrate cartridges, this apheresis system was coupled to Sepharose® gel columns in parallel, one of which contained monoclonal human anti TNF-R1 and the second anti TNF-R2. The concept of affinity chromatography preparations has been technically available for protein separation and purification, and improved upon over the past 30 years, Ey, P. L., et al., Isolation of pure IgG1, $IgG_{2a}$, and $IgG_{2b}$, immunoglobulins from mouse serum using protein A-Sepharose, *Immunochemistry* 1978; 15:429-436. This type of device represents one of the few examples of linking in vivo production of TNF inhibitors to in vitro removal and return of the purified extracted plasma to the patient to prevent fluid reduction.

The patient is a 55 year old Russian gentleman with metastatic melanoma. The patient smoked 2-3 packs of cigarettes a day for some 20 years. He quit this habit several years ago. He was also a heavy alcohol user in years past but had decreased his intake to 1-2 glasses of wine a day. Review of his medications on this date revealed methylprednisolone 4 mg in AM and 4 mg in PM. Apparently this was being taken as replacement therapy for adrenal cortical suppression that was graded iatrogenically at the time of the treatment of his alveolitis (see below). He was additionally taking narcotic analgesics. As a child he suffered the usual childhood diseases, denies rheumatic fever, scarlet fever or diphtheria. As an adult he has had no major medical illnesses save those described above. He has had no other major surgeries in the past and has no known allergies.

His history of present illness began in November of 1995 when he noted growth of a right facial naevus which bled and enlarged over the period of one year. This was treated initially by cryotherapy. It regrew within two months and was excised. Histology was that of a malignant melanoma (Clark's level unknown). Staging work up at the time was negative and included CT scans of the head, neck, chest and abdomen. He remained disease free until March of 1996 when he developed right cervical and right submental adenopathy. Preoperative CT scan of the head, neck, chest and abdomen confirmed the right cervical adenopathy but revealed no other sites of metastases. In June of 1996 he underwent re-excision with a right radical neck dissection. In this material, one lymph node was histologically confirmed to involve melanoma. The patient was treated with a course of Vindesine 3 $mg/m^2$ every three weeks, Dacarbazine 100 $mg/m^2$ every three weeks for four cycles. He subsequently developed cutaneous metastases in the skin of his left shoulder, multiple metastases to the scars within the left anterolateral neck and multiple axillary metastases treated with fifteen subsequent excisions of recurrent metastases. In March of 1999 he was offered a trial of Interleukin-2 but on this developed severe pulmonary toxicity that had a protracted course and was diagnosed as idiopathic fibrosing alveolitis. Interleukin-2 was discontinued and he received radiation therapy to his right neck and axilla for six weeks beginning in the month of May 1999. He developed low back pain in August of 1999. Work up in October of 1999 revealed bone metastasis of the vertebral body of T-11 and subsequent MRI revealed a lytic destructive process in the right transverse process and pedicle of the $11^{th}$ thoracic vertebra, as well as complete replacement of the vertebral body at T-11. Additional metastases were appreciated in the vertebral body of the $9^{th}$ thoracic vertebral as well as the $10^{th}$. Also there was involvement of L-1 and L-2 vertebral bodies. Tumor seen again on the Mar. 16, 2000 MRI revealed growth posteriorly from the mid body of the $11^{th}$ thoracic vertebral into the spinal canal by 7.4 to 7.8 mm with posterior displacement of the spinal cord. CT scan of the chest, abdomen and pelvis revealed possible multiple liver metastases but no other suggestion of visceral metastases.

The patient was then considered for a trial of UltraPheresis™ in an effort to reduce solubilized receptors to tumor necrosis factor, both sTNF-R1 and sTNF-R2. As facilities for the application of this form of semi-selective plasma exchange did not exist in Moscow at this time, affinity column separation of inhibitors was explored. Monoclonal antibodies against sTNF-R1 and R2 delivered to the Cardiology Research Center in Moscow for Dr. Sergei N. Petrovsky, PhD, head of the group for Affinity Sorbents for Medicine, Pocard, Ltd, 3-rd Cherepkovskaya str., 15a, Moscow, 121552, Russia. Ninety milligrams of anti sTNF-R1 monoclonal antibody and 180 mg of anti sTNF-R2 monoclonal antibody were then bound with sterile Sepharose® using cyanogen bromide in a glass column previously described for use in the lipopack cholesterol absorbent column technology. The particular methodology used is well described and is commercially available in Russia for the development of these LDL absorbent columns. The columns were prepared under sterile conditions in a GSIO 9,001 facility. They were subjected to endotoxin testing, viral, fungal and bacterial cultures, and prepared for human use under written Informed Consent and under approval of the Kremlin President's Hospital Medical Center.

On May 2, 2000 the patient's physical examination was that of a well-developed, well-nourished male who appeared his stated years. Examination of his head revealed a normal hair distribution and texture. His tympanic membranes and external auditory canals were clear. The sclerae and conjunctivae were clear. The pupils were round, reactive to light and accommodation. EOM intact. Funduscopic examination was normal. He had a healed graft over his right inferior cheek and extensive scarring over the right anterolateral neck consistent with his history of prior right radical neck dissection. There were no demonstrable pathologic masses within the skin, the scar, or pathologic nodes appreciated either in the cervical nodes or the supraclavicular fossae bilaterally. His lungs were clear to ausculation and percussion. His precordium demonstrated a non-displaced PMI, a normal S1 and S2 without gallop, murmur or rub. With the right arm exhibited there was 3+lymphedema. The right axilla was poorly examined due to extensive scarring in that area but no palpable nodes were appreciated. His abdomen was mildly obese. His liver and spleen were normal to physical examination. His axillary lymphatics were unremarkable. The genitalia was that of a normal mature male without pathologic mass. The lower extremities revealed no edema, cyanosis or clubbing and exhibited full ROM. His neurologic examination included a normal mental status. Cranial nerves 2-12 were intact. His DTR's were 2+ and symmetric. Motor and sensory testing was normal. His cerebellar examination revealed no dysmetria, dysarthria or dysdiadochokinesia. He was essentially confined to bed due to back pain only, but was able to roll from left to right without assistance. He had been confined to a wheelchair for the antecedent two months due to back pain and was wearing a back brace which was removed for physical exam.

His laboratory parameters included a hemoglobin of 8.8 gms, WBC 2,800 with normal differential. His platelet count was 121,000. The comprehensive metabolic panel was unremarkable and alkaline phosphatase was normal.

An MRI scan of the patient's 11th thoracic vertebral body revealed a mass placing pressure on the spinal cord. This was taken during the week prior to intensive therapy started in April of 2000 and continuing through May.

On the first day an 18 gauge plastic cannula was inserted in the left antecubital vein. A second was established in the right greater saphenous vein of the leg. The patient was connected to a standard Cobe Spectra centrifically based plasma separator. Six hundred cc's of plasma was then harvested and replaced with 5% albumin in saline. The patient's plasma was then pumped over column one which contained 45 mg of anti sTNF-R1 monoclonal antibody and then passed to column two which contained 90 mg of anti sTNF-R2 monoclonal antibody. The material eluted from the column was then analyzed for the level of each inhibitor still in the plasma and 50 cc's of that plasma was then injected into the patient at the end of pheresis to look for any febrile reactions or allergic reactions. He tolerated this with no apparent clinical adverse effect.

Subsequent analyses of the patient's plasma and the eluate of the column revealed that the column was able to capture essentially all of the inhibitor presented to it in this 600 ml plasma volume. The patient was maintained in the hospital over night and on the morning of the 4th of May, he was brought from hospital room back to the apheresis suite. He had a comfortable evening and ate a normal dinner and breakfast. The IV's were re-established in the same sites. The patient was re-attached to the Cobe Spectra machine and on this date, 3 liters of plasma was harvested and delivered to the columns as described above in a continuous fashion until 3 liters of plasma was treated.

His R1 level before treatment was 1500 and after treatment was 1450. His R2 level before treatment was 5000 and after treatment was 3800 on this date. Again he tolerated the procedure well with no clinical adverse effect and no increase in pain in his back.

On the third day the 6th of May, the treatment was repeated. Three liters of plasma were again pheresed over the columns in an identical fashion as described above. His pretreatment R1 was 2300, post treatment R1 was 1600. Pretreatment R2 was 5200, post treatment R2 was 3200. At the end of each treatment the columns were washed with glycine buffer at a pH of 2.5 to elute the bound inhibitor from them and measure them quantitatively. It was determined that at these amounts of treated plasma the columns were not saturated and significant quantities of inhibitor removed.

His fourth treatment was on the 7th of May. He was increased to 4 liters of treated plasma. The procedures were repeated each day with gradual escalations in amount of plasma treated to a maximum treated plasma of 8 liters on the May 10th, 11th, 12th, 13th, and 14th. On May $16^{th}$, two columns were used in parallel, thus increasing the amount of plasma delivered to each column remained at 30 mls per minute, for a total of 60 mls of plasma per minute. This resulted in a pretreatment R1 of 2600 and a post treatment of 1700. R2 pretreatment was 4250 and went to post treatment of 2700.

He was subsequently treated with 8 liters of plasma a day using the double column method. On the 21st of May he had a repeat CAT scan of his spine which revealed complete resolution of tumor. Three days after that, May 24th, he had a repeat MRI which was compared to the pretreatment MRI and confirmed a complete response. The patient was followed carefully in the hospital by his attending physicians as well as attending neurosurgeons, who followed him on a daily basis concerned about tumor bleeding or tumor swelling in his tight and anatomically dangerous places but fortunately the patient enjoyed a complete response with no apparent adverse effect.

For the details of daily treatment in terms of volumes, columns, blood flow rates and plasma flow rates see Table 1.

The patient has enjoyed an apparent complete response without any significant adverse effect. He was able to get up and walk after the fourth procedure. Two additional courses were planned in an endeavor to consolidate this response. This case is consistent with the observations that a salutatory tumor response can be achieved in melanoma by removing solubilized receptors to TNF. This column is so specific that it removes only sTNF-R1 and R2 and that is the only explanation for the response that this man has had from an oncologic point of view. A profound column yield was observed on the third treatment day for sTNF-R2 with modulation for the remaining treatment days throughout this fifteen day course. R1 peaked on treatment day 7 with the total amount removed of 6 million pg. This also modulated throughout the course of treatments but never approached the 16 million mark set by sTNF-R2.

Radiographic examination on the day following his first fifteen day course of apheresis with anti R1 and anti R2 affinity column extraction revealed no melanoma and considerable reduction of the lesion at the 4th lumbar vertebral body. Currently the patient remains active, with good appetite, is walking normally and his back pain is much improved. He has positive anticipation for his second course of apheretic treatments.

Example 4

Production of Polyclonal Antibodies to STNF R1 and R2; Preparation of Column for Treatment of Patients Polyclonal antibodies were produced in New Zealand white rabbits injected with recombinant antigen, soluble tumor necrosis factor receptor ("STNF") R1 and R, injected into the rabbit on a standard immunization protocol, then boosted. 200 mg of polyclonal antibody may be produced against STNF R1 and R2, per liter. The animals will be bled monthly. 200 mg of antibody can be bound safely to 200 mg of AH SEPHAROSE™ beads. The binding is done with ethanolamine and periodate. Binding is therefore excellent. This matrix is then placed in a 200 mg polycarbonate column. Each step is done in an aseptic fashion and the final product is then terminally sterilized with standard radiation protocols and subjected to USDA standard testing for pyrogen and infectious agents.

This amount of antibody is enough to remove STNF R1 and STNF R2 in human extracellular water sufficient to reduce the level of 10,000 pg per ml to under 1,000 pg per ml in two to three hours of plasma exchange.

The use of the columns to reduce inhibitor levels to less than 1000 pg/ml over a period of at least three weeks has resulted in remissions of between 40 and 90% in non-small cell lung cancer, breast cancer and melanoma patients. It is therefore predictable that the treatment results in a rather consistent tumor specific inflammatory response and the majority of patients having the most common tumor types, including breast, small cell lung, colon, ovarian, hepatic, melanoma, and renal cell carcinoma as well as ovarian and endometrial cancers should respond to the treatment. In combination with antibodies against vascular endothelial growth factor receptor and/or epidermal growth factor receptor and/or antibodies against fibroblast derived growth factor and transforming growth factor receptor, either singularly or in combination, the treatment is expected to produce excellent responses in these tumor types and may play a role in the clinical management of hematopoietic disorders as well.

The methods and systems disclosed herein are useful for treatment of patients with cancer, immune-mediated disorders, chronic parasitism, some viral diseases especially viral diseases such as HIV which cause immunosuppresion, and other disorders characterized by elevated levels of TNF receptors or inhibitors to IL-2, IL-6, gamma interferon, or other pro-inflammatory signals as well as white cell activation. An example demonstrates efficacy in treating a cancer patient.

Modifications and variations of the method and compositions described herein will be obvious to those skilled in the art. Such modifications and variations are intended to come within the scope of the appended claims.

I claim:

1. A method of enhancing an immune response in a patient having soluble cytokine receptor molecules in the blood which inhibit the immune response, the method comprising:
    (a) obtaining whole blood from the patient;
    (b) separating plasma from the blood;
    (c) contacting the plasma with at least one cytokine receptor inhibitor selected from the group consisting of antibodies or antibody fragments binding to soluble cytokine receptor molecules, and cytokine molecules or epitopes thereof binding to soluble cytokine receptor molecules;
    (d) removing soluble cytokine receptor molecules bound to the cytokine receptor inhibitor from the plasma; and
    (e) returning the plasma from which the soluble cytokine receptor molecules have been removed to the patient.

2. The method of claim 1, wherein the cytokine receptor inhibitor is immobilized in a solid support or membrane.

3. The method of claim 1, wherein the antibodies are recombinant.

4. The method of claim 1, wherein the antibodies are in a mixture of antibodies immunoreactive with the soluble cytokine receptor molecules.

5. The method of claim 1, wherein the patient is human.

6. The method of claim 1, wherein the soluble cytokine receptor is selected from the group consisting of soluble receptors for tumor necrosis factors alpha and beta.

7. The method of claim 1, wherein the soluble cytokine receptor molecule is a TNF receptor.

8. The method of claim 1, wherein the antibodies or antibody fragments are monoclonal.

9. The method of claim 1, wherein the monoclonal antibodies or antibody fragments are recombinant.

10. The method of claim 1, wherein the plasma is contacted with antibodies or antibody fragments.

11. The method of claim 1, wherein the plasma is contacted with polyclonal antibodies or antibody fragments.

12. The method of claim 1, wherein the plasma is contacted with monoclonal antibodies or antibody fragments.

13. The method of claim 1, wherein the plasma is contacted with the cytokines or cytokine epitopes.

14. The method of claim 12, wherein the monoclonal antibodies or antibody fragments are recombinant.

15. The method of claim 1, wherein the blood is separated into plasma by filtration.

16. The method of claim 15, wherein the filtration is ultrafiltration.

17. The method of claim 1, wherein the method is repeated.

* * * * *